(12) United States Patent
Stenzler et al.

(10) Patent No.: US 11,638,798 B2
(45) Date of Patent: May 2, 2023

(54) NASAL CANNULA SYSTEMS AND METHODS

(71) Applicant: Vyaire Medical Capital LLC, Mettawa, IL (US)

(72) Inventors: Alex Stenzler, Long Beach, CA (US); Steve Han, Huntington Beach, CA (US)

(73) Assignee: Vyaire Medical Capital, LLC, Mettawa, IL (US)

( * ) Notice: Subject to any disclaimer, the term of this patent is extended or adjusted under 35 U.S.C. 154(b) by 584 days.

(21) Appl. No.: 16/341,864

(22) PCT Filed: Oct. 12, 2017

(86) PCT No.: PCT/US2017/056384
§ 371 (c)(1),
(2) Date: Apr. 12, 2019

(87) PCT Pub. No.: WO2018/071699
PCT Pub. Date: Apr. 19, 2018

(65) Prior Publication Data
US 2019/0240438 A1 Aug. 8, 2019

Related U.S. Application Data

(60) Provisional application No. 62/407,980, filed on Oct. 13, 2016.

(51) Int. Cl.
*A61M 16/06* (2006.01)
*A61M 16/08* (2006.01)
*A61M 16/20* (2006.01)

(52) U.S. Cl.
CPC .... *A61M 16/0666* (2013.01); *A61M 16/0622* (2014.02); *A61M 16/0683* (2013.01); *A61M 16/0858* (2014.02); *A61M 16/209* (2014.02)

(58) Field of Classification Search
CPC A61J 11/0005; A61M 16/00; A61M 16/0003; A61M 16/0051; A61M 16/0057;
(Continued)

(56) References Cited

U.S. PATENT DOCUMENTS 4,054,133 A * 10/1977 Myers .................. A61M 16/20
128/204.26
4,989,599 A * 2/1991 Carter ............... A61M 16/0666
128/207.18

(Continued)

FOREIGN PATENT DOCUMENTS

| DE | 10322964 A1 | 12/2004 |
|---|---|---|
| FR | 2827778 A1 | 1/2003 |
| WO | WO-2011029073 A1 | 3/2011 |

OTHER PUBLICATIONS

International Search Report and Written Opinion for Application No. PCT/US2017/056384, dated Dec. 19, 2017, 10 pages.

*Primary Examiner* — Annette Dixon
(74) *Attorney, Agent, or Firm* — Morgan, Lewis & Bockius LLP

(57) ABSTRACT

A nasal interface is provided that can allow for delivery of flow of a gas to a patient for respiratory support while preventing injury or irritation to the patient. The nasal interface can include a nasal pillow set having a nasal pillow, which can engage against a nose, and relief port, which can permit a gas to be released from the nasal interface. A nasal cannula can include a cannula body to direct a gas through the nasal interface, and can have an opening to direct a gas out of the cannula body. The gas can be directed from the cannula body, through the opening, toward a nasal pillow and a patient's nare. The nasal interface can be coupled with a head harness, which can be worn on the patient's head, and can include a guide that extends toward the nasal interface.

20 Claims, 11 Drawing Sheets

(58) Field of Classification Search
CPC .......... A61M 16/0063; A61M 16/0066; A61M 16/0069; A61M 16/021; A61M 16/024; A61M 16/0493; A61M 16/0666; A61M 16/0672; A61M 16/0677; A61M 16/0683; A61M 16/0694; A61M 16/0825; A61M 16/085; A61M 16/0858; A61M 16/107; A61M 16/1075; A61M 16/109; A61M 16/1095; A61M 16/12; A61M 16/125; A61M 16/127; A61M 16/142; A61M 16/16; A61M 16/18; A61M 16/20; A61M 16/203; A61M 2016/0024; A61M 2016/0027; A61M 2016/1025; A61M 2016/103; A61M 2202/0208; A61M 2205/18; A61M 2205/3331; A61M 2205/3334; A61M 2205/3368; A61M 2205/3379; A61M 2205/3653; A61M 2205/50; A61M 2210/0618; A61M 2230/005; A61M 2230/42; A61M 2230/432; A61M 2230/435; A61M 2230/50; A61M 2240/00
See application file for complete search history.

(56) References Cited

U.S. PATENT DOCUMENTS

| | | | |
|---|---|---|---|
| 2003/0200970 A1* | 10/2003 | Stenzler | A61M 16/0825 128/207.18 |
| 2004/0016432 A1* | 1/2004 | Genger | A61M 16/0672 128/204.18 |
| 2007/0107737 A1* | 5/2007 | Landis | A61M 16/0003 128/207.18 |
| 2007/0175473 A1* | 8/2007 | Lewis | A61M 16/085 128/204.18 |
| 2011/0125052 A1 | 5/2011 | Davenport et al. | |

* cited by examiner

NASAL CANNULA SYSTEMS AND METHODS

CROSS-REFERENCE TO RELATED APPLICATIONS

This application is the U.S. National Phase under 35 U.S.C. § 371 of International Application No. PCT/US2017/056384, filed on Oct. 12, 2017, which claims the benefit of and priority to related U.S. Provisional Patent Application No. 62/407,980, filed on Oct. 13, 2016, the entirety of each of which is incorporated herein by reference.

BACKGROUND OF THE DISCLOSURE

The present description relates in general to ventilation devices, and more particularly, for example, without limitation, to nasal cannula systems and methods.

Nasal cannula devices deliver a flow of a gas to a patient for respiratory support. A flow of gas, such as oxygen, can be delivered to a patient's nares at a rate of 1-5 litres per minute. In some instances, a high flow nasal cannula can be used to deliver a flow of gas of up to 60 litres per minute to a patient's nares.

A flow of gas delivered to the nares of a patient can create problems if excess gas is not permitted to escape the patient's respiratory system. For example, a nasal cannula device, used to deliver the gas to the patient, may occlude the nares and thereby prevent the release of excess gas from the patient's respiratory system. The excess gas can increase the pressure within the patient's lungs to an unsafe level and thereby cause injury. Although any patient can be subject to injury, newborn babies are particularly susceptible to injury due to excess pressure within their respiratory system.

The description provided in the background section should not be assumed to be prior art merely because it is mentioned in or associated with the background section. The background section may include information that describes one or more aspects of the subject technology.

SUMMARY

The present disclosure provides various new methods and device concepts for delivery of flow of a gas to a patient for respiratory support while preventing injury or irritation to the patient, including for example, preventing injury to a nose, lungs, and ears.

In accordance with some embodiments disclosed herein, a nasal interface is provided that can seal against a patient's nose and which can reduce the required contact force for positioning the nasal interface. In some embodiments a nasal interface is provided that can permit a permit a partial seal between the nasal interface and the patient's nares. Accordingly, in some embodiments, a nasal interface is provided that can facilitate a flow of gas toward the patient to maintain a desired therapeutic pressure target while preventing injury to any of a respiratory system, airway, and septum In some embodiments disclosed herein, a nasal interface is provided that can include a nasal pillow configured to engage a nose to fluidly coupled to the nasal pillow with a nostril of the nose, and a prong that is fluidly coupled to the nasal pillow to direct a gas toward the nasal pillow. Further, some embodiments include a relief port of the nasal pillow to permit a gas to be released from the nasal pillow, which can prevent injury to any of the patient's respiratory system, airway, and septum.

Some implementations of the present disclosure provide, a nasal interface comprising a pillow body comprising a nasal pillow having an pillow opening and a pillow cavity that extends from the pillow opening into the nasal pillow, wherein the nasal pillow is configured to engage a nose to fluidly coupled to the pillow cavity with a nostril of the nose; a cannula body comprising a prong that extends into and is fluidly coupled to the pillow cavity; a pressure monitoring port fluidly coupled to the pillow cavity; and a pressure relief port coupled to the pillow cavity.

Some embodiments of the present disclosure provide, a nasal interface assembly comprising a nasal interface comprising: a pillow body comprising a nasal pillow having an pillow opening and a pillow cavity that extends from the pillow opening into the nasal pillow, wherein the nasal pillow is configured to engage a nose to fluidly couple the pillow cavity with a nostril of the nose; a cannula body comprising a prong coupled to the pillow cavity, wherein the prong is configured to direct a gas out of the cannula body; a pressure monitoring port fluidly coupled to the pillow cavity; and a pressure relief port coupled to the pillow cavity; and a gas supply line fluidly coupled to the cannula body; and a pressure sense line fluidly coupled to the pressure monitoring port.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various implementations and is not intended to represent the only implementations in which the subject technology may be practiced. The appended drawings are incorporated herein and constitute a part of the detailed description. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

The present disclosure addresses several challenges encountered in nasal cannula systems and methods. Numerous improvements are disclosed that permit the delivery of flow of a gas to a patient for respiratory support while preventing injury or irritation to the patient, including for example, preventing injury to a nose, lungs, and ears.

For example, in accordance with features of the present disclosure, various features and advantages of a nasal interface and mounting head harness can deliver a gas to a patient. The disclosed nasal cannula system and methods can permit monitoring of an air pressure at a nasal interface, release air pressure from a nasal interface, and reduce the pressure exerted by a nasal interface and/or mounting head harness against the patient.

Referring to the figures, nasal cannula systems and methods can include any of a nasal interface 100 and a mounting head harness 500.

Figure 1:
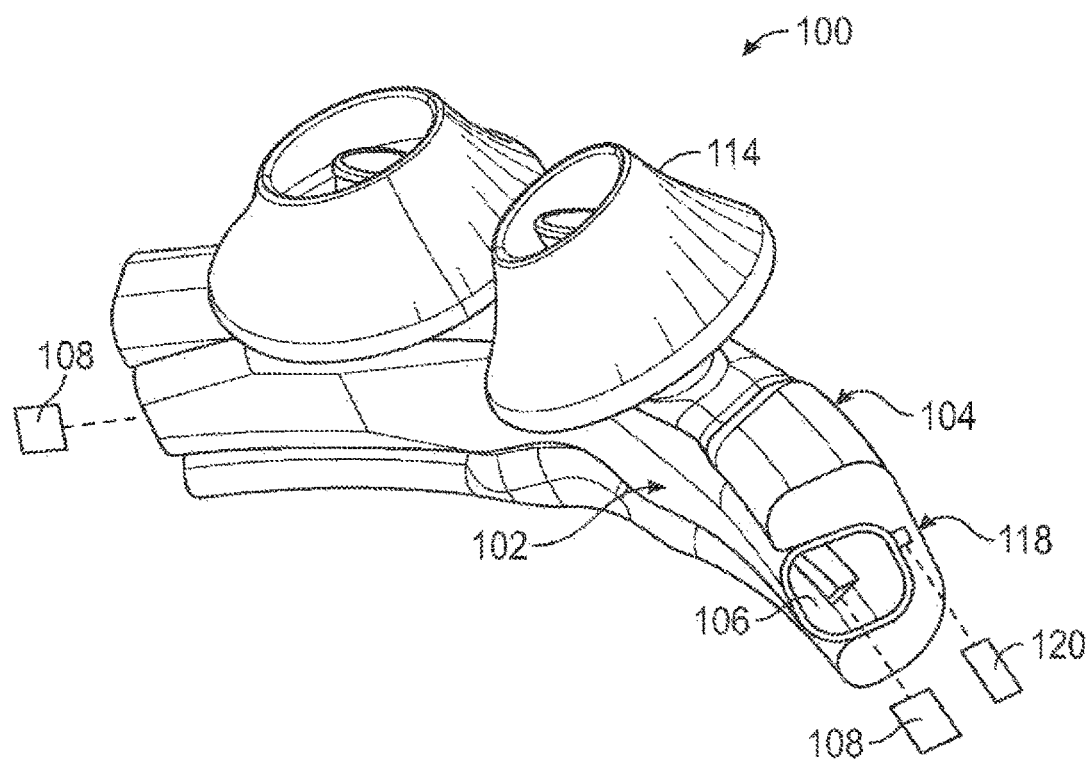
FIG. 1 illustrates a perspective view of a nasal interface, according to some embodiments.
Figure 2:
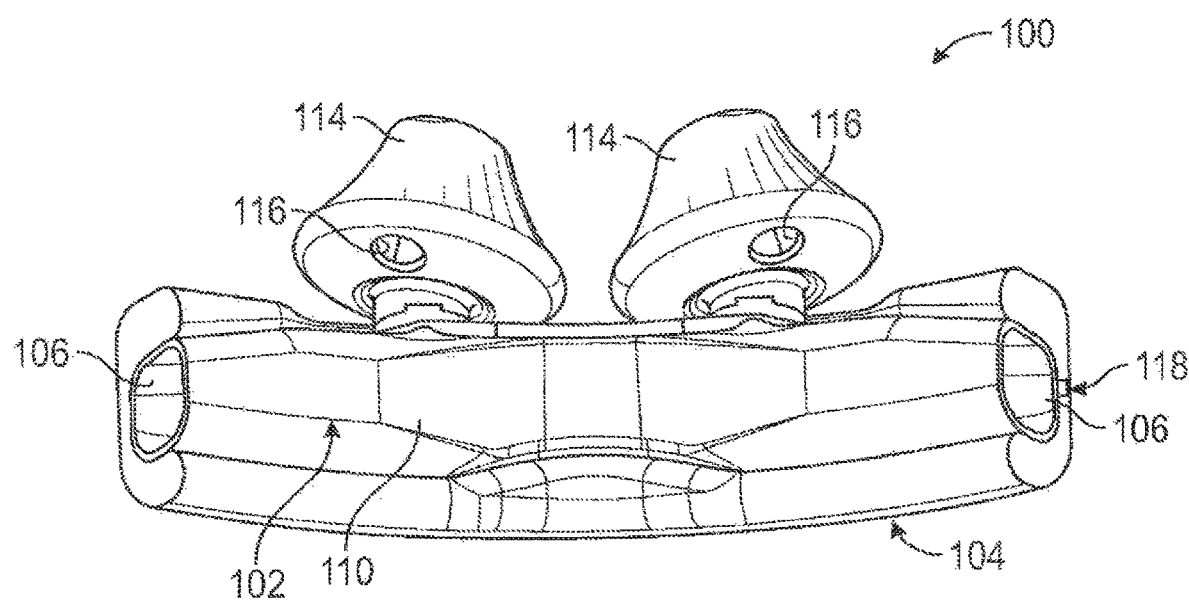
FIG. 2 illustrates a rear view of a nasal interface, according to some embodiments.

Referring to FIGS. 1 and 2, a nasal interface 100 can comprise a nasal cannula 102 and a nasal pillow set 104. The nasal interface 100 can comprise a gas port 106 to receive and direct a gas toward a patient's nares, i.e., the pair of nostrils or openings of the nasal cavity that extend through the nose. The gas port can be any of an opening and passage through the nasal cannula 102 to permit a fluid to move therethrough. The gas port 106 can be coupled to a gas connector 108, shown here schematically. The gas connector 108 can be fluidly coupled to a gas supply line to direct a gas and/or combination of gases, e.g., oxygen, to the nasal interface 100. In some embodiments, the gas port 106 can comprise the gas connector 108.

The nasal interface 100 can comprise two gas ports 106. The gas ports 106 can be positioned such that opposing end portions of the nasal interface 100 include a gas port 106. Any of the nasal cannula 102 and the nasal pillow set 104 can comprise a gas port 106. A gas port 106, can receive a gas into, or permit a gas to move out of, any of the nasal cannula 102 and the nasal pillow set 104. A gas can be received into a portion of the nasal cannula 102 comprising a cannula body 110. The cannula body 110 can include an opening to permit a gas to be directed out of the cannula body 110. In some embodiments of the present disclosure, the gas is directed from the cannula body 110, through the opening, toward any of a nasal pillow and a patient's nare.

The opening of the cannula body 110 can comprise a prong 112 that extends away from the nasal cannula 102. A gas can move from the cannula body 110 toward the prong 112. The prong 112 can be configured with a shape and orientation to direct the gas toward a patient's nares. In some embodiments of the present disclosure, the prong 112 can extend into a nasal pillow 114 configured to engage a patient's nose. The nasal interface 100 can comprise a pair of nasal pillows 114, each nasal pillow 114 comprising a prong 112. The nasal interface 100 can comprise a first and second prong 112 that extend into a first and second nasal pillow 114, respectively.

The nasal interface 100 can comprise a pressure relief port 116 to permit the release of excess gas. The pressure relief port 116 can release a gas from the nasal interface 100 and/or an airway of a patient using the device. Each nasal pillow 114 can comprise a pressure relief port 116 and can be configured to release a gas from a cavity of the nasal pillow 114. The pressure relief port 116 can prevent injury to any of the patient's respiratory system, airway, and septum. In some embodiments, the nasal interface 100 can comprise a plurality of pressure relief ports. For example, each nasal pillow 114 can comprise two or more pressure relief ports. In some devices of the present disclosure, any of nasal cannula 102 and the nasal pillow set 104 comprise a pressure relief port.

Figure 13:
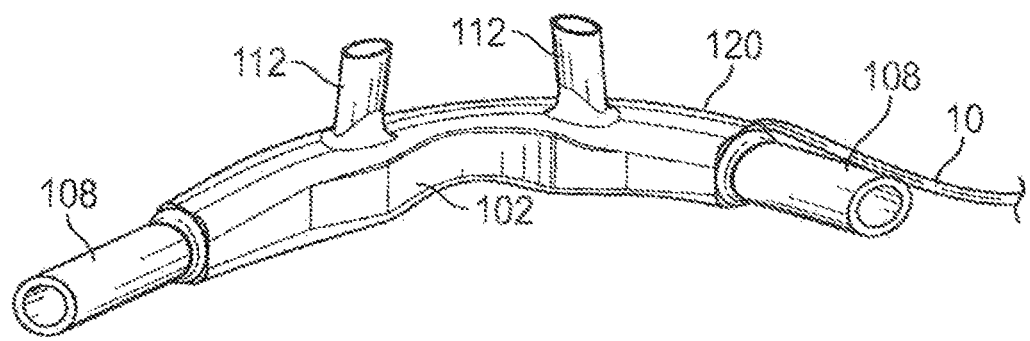
FIG. 13 illustrates a perspective view of a nasal cannula and gas connectors, according to some embodiments.
Figure 14:
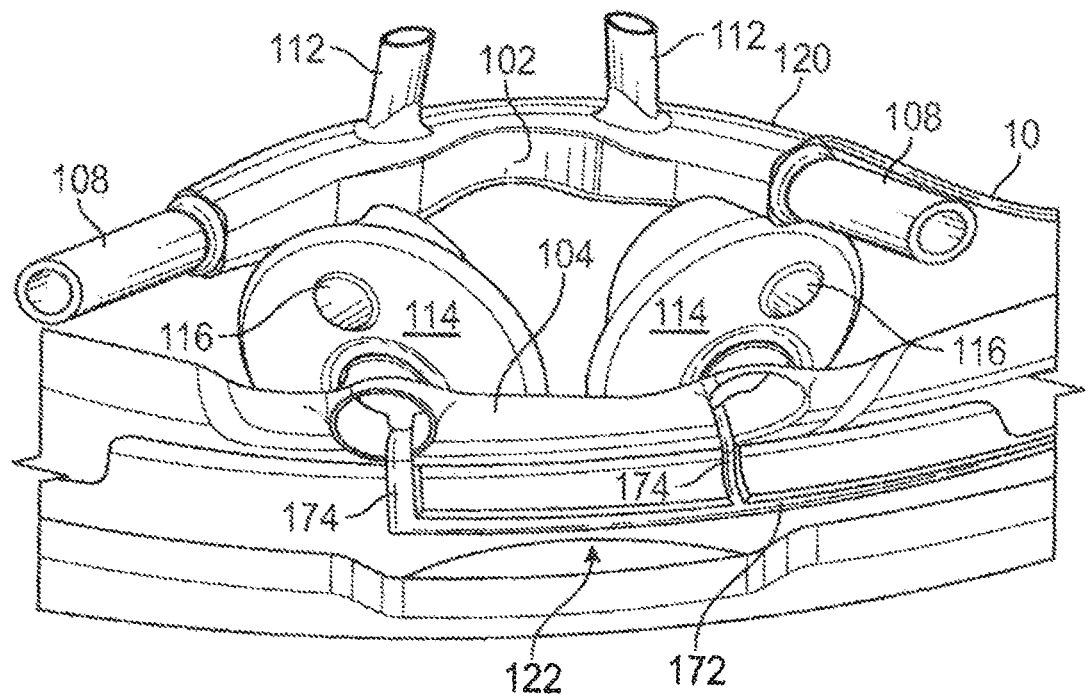
FIG. 14 illustrates a detail view of a nasal cannula, a nasal pillow set, and gas connectors, according to some embodiments.
Figure 15:
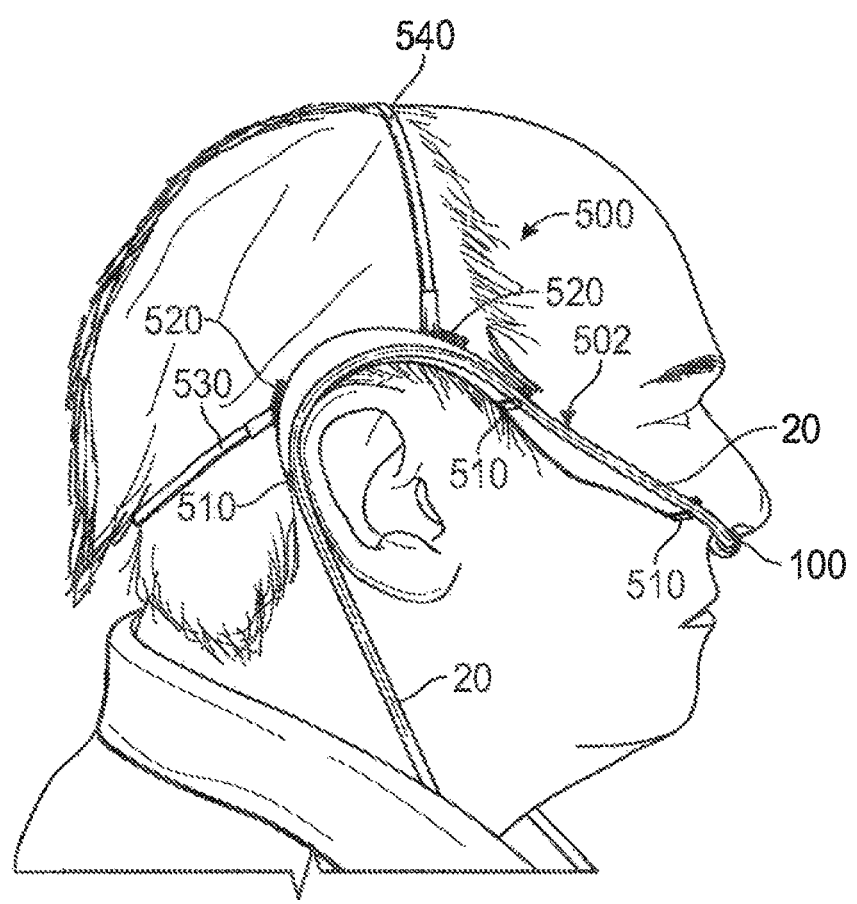
FIGS. 15-19 illustrate a mounting head harness, according to some embodiments.
Figure 16:
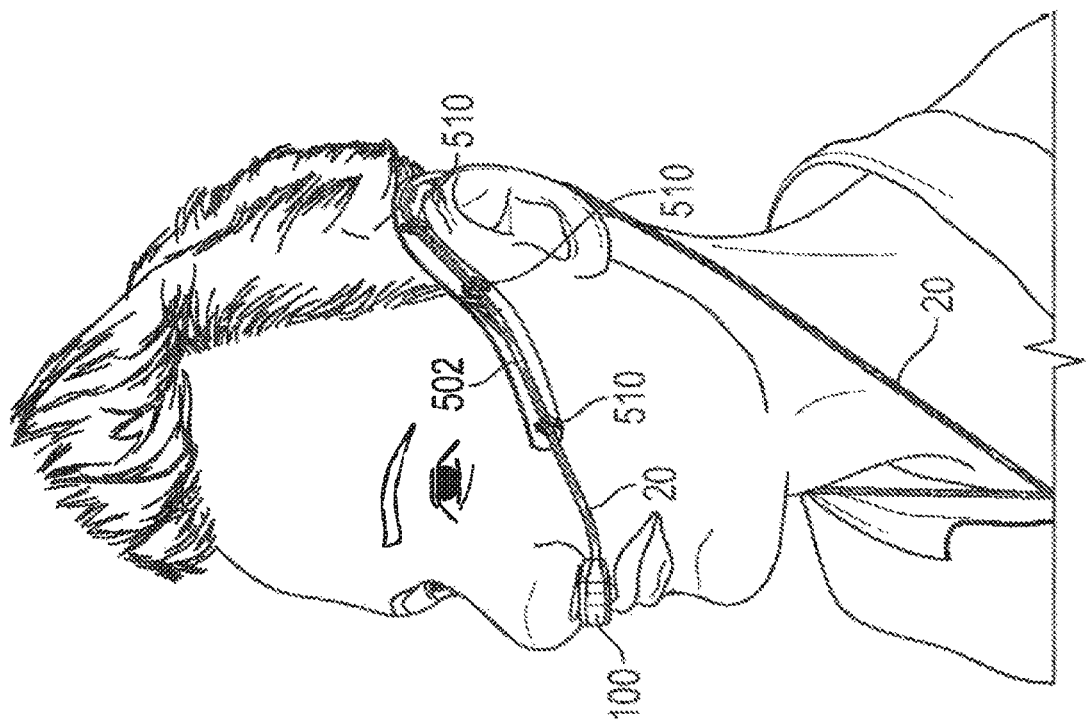
Figure 17:
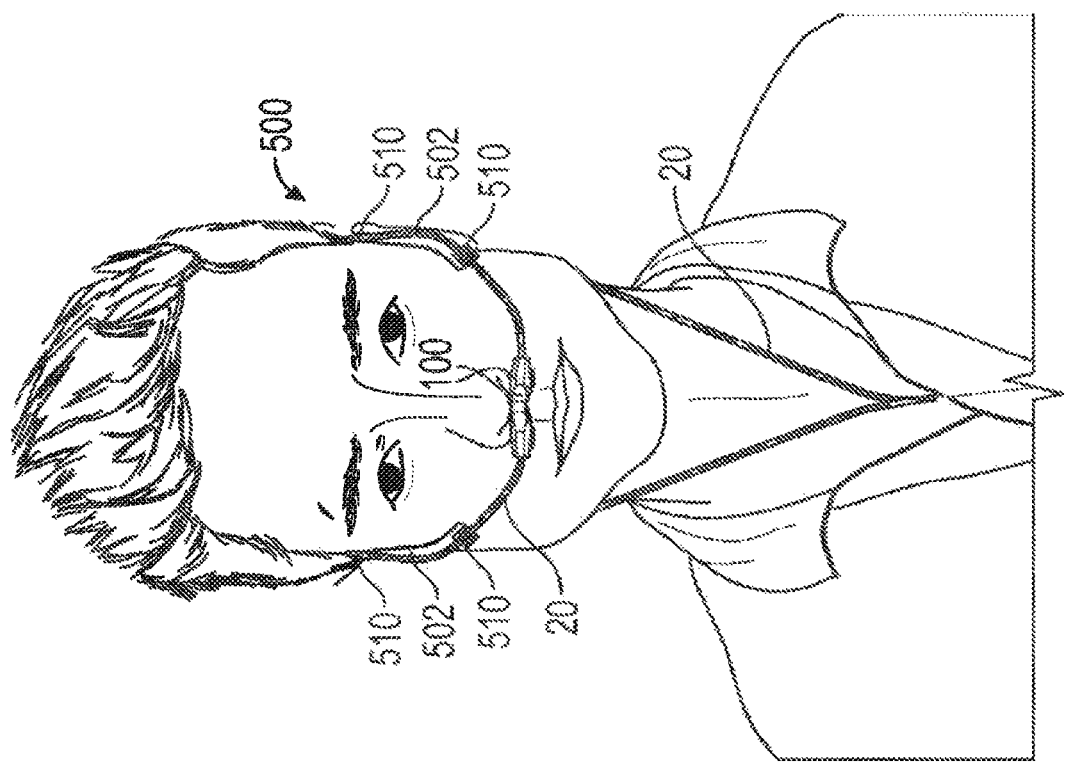
Figure 19:
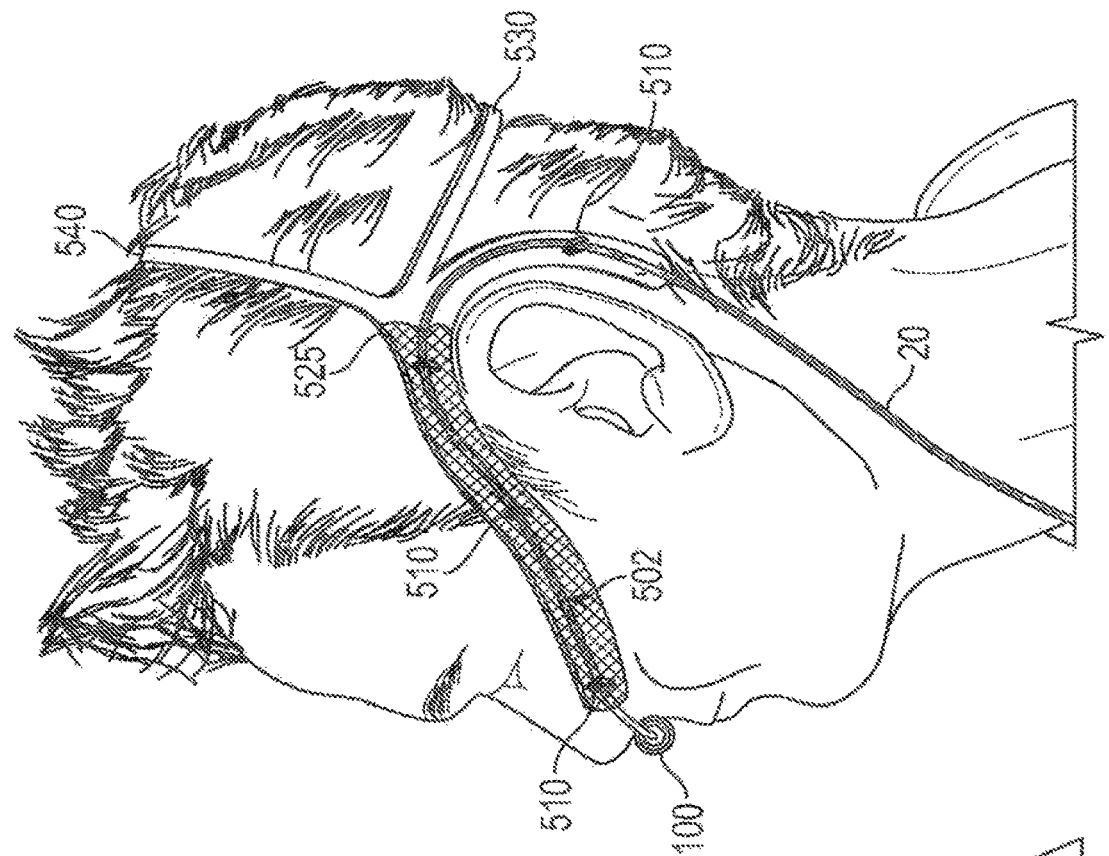
Figure 18:
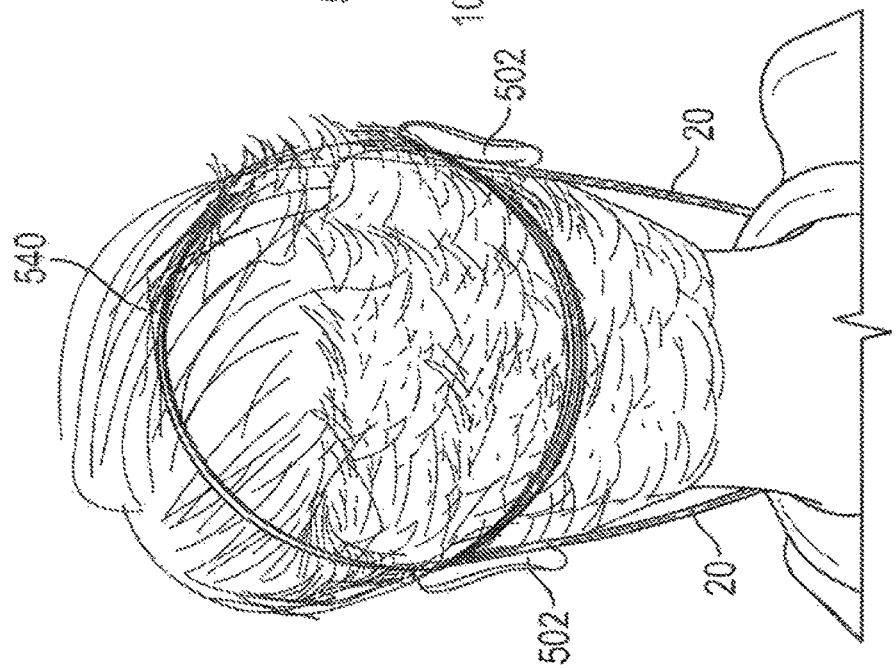

The nasal interface 100 can comprise a monitoring port 118 to permit the monitoring of a pressure. The monitoring port 118 can be fluidly coupled to a portion of the nasal interface 100 to permit monitoring of a pressure at any portion of the nasal interface 100. The monitoring port 118 can be fluidly coupled the nasal interface 100 to permit monitoring of any of the cannula body 110, a prong 112, and a nasal pillow 114. The monitoring port can be coupled to a pressure sense connector 120, illustrated in FIGS. 13 and 14, and schematically in FIG. 1. The pressure sense connector 120 can be coupled to a pressure sense line 10 to permit monitoring of a pressure at any of a nasal cavity, airway, and lung of a patient. The pressure monitoring can be used to titrate or close-loop control a flow of gas to the nasal interface 100, to create and/or set a pressure, and/or indicate an alarm condition. The pressure monitoring can be used to engage an alarm to indicate a cannula disconnection or obstruction, or excessive pressure.

Figure 3:
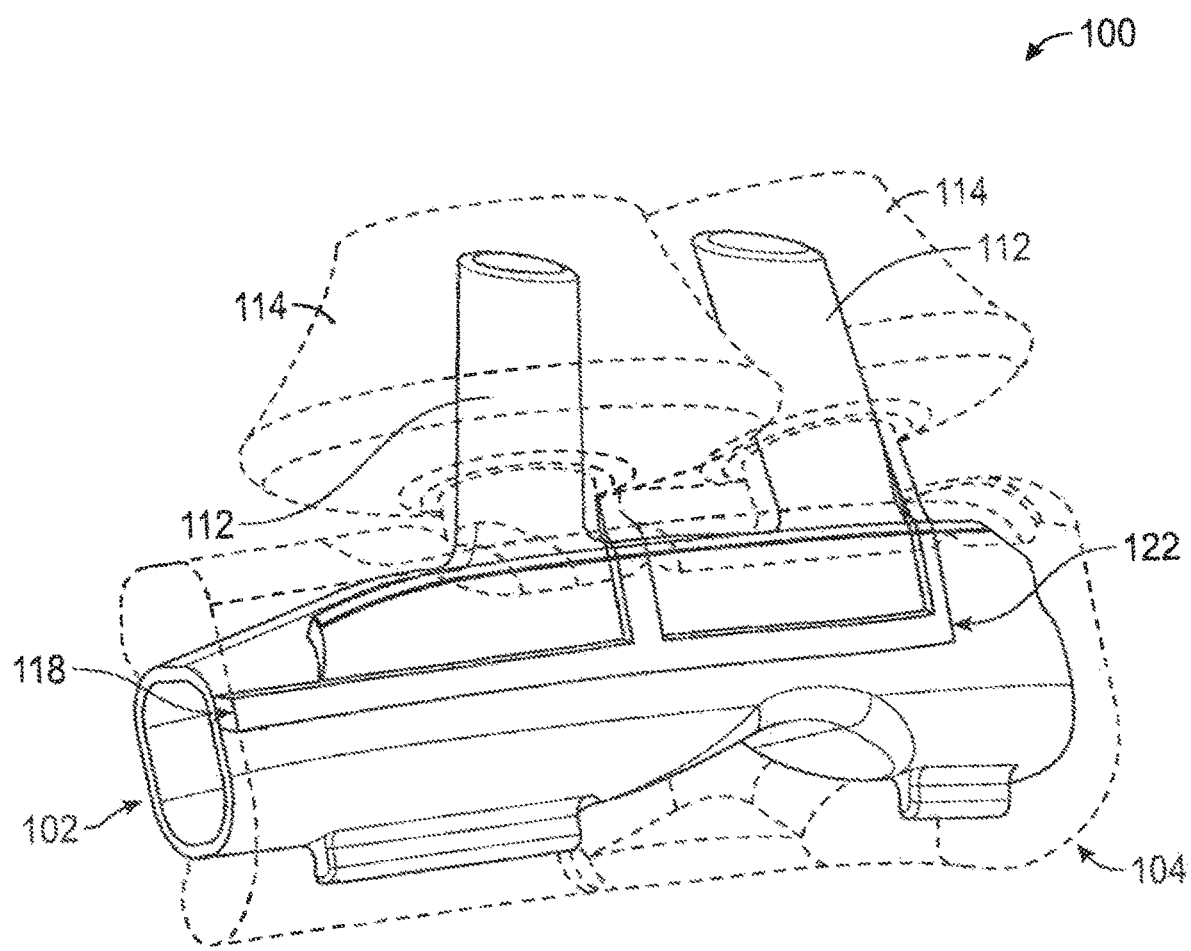
FIG. 3 illustrates a front view of a nasal interface, according to some embodiments.

Referring to FIG. 3, the monitoring port 118 can comprise a pressure passage 122 coupled to a nasal pillow. A portion of a pressure passage 122 can be coupled to a cavity of the first and second nasal pillow 114. In some aspects, the pressure passage 122 is fluidly coupled to a cavity of the first and second nasal pillows 114, and can extend between the prong 112 and the nasal pillow 114.

The nasal pillows 114 are configured to engage a portion of a nose to form a seal between the nasal interface 100 and the patient's nose. The nasal pillows 114 can engage a portion of the nose that proximal to the nares, such that the nasal interface 100 and a passage of the nares is fluidly coupled. The nasal interface 100 of the present disclosure can permit a partial seal between the nasal pillows 114 and the patient's nares, which can reduce the required contact force for positioning the nasal interface 100 with the patient. Any leakage of gas around a nasal pillow 114 can be compensated by increasing a flow of gas toward the patient to maintain a desired therapeutic pressure target.

The nasal interface 100 can comprise one or more removably coupled portions. The interchangeable portions can comprise, for example, a nasal cannula 102 and a nasal pillow set 104, illustrated in wireframe in FIG. 3. In some embodiments of the present disclosure, any of the nasal cannula 102, the pillow set 104, the nasal pillow 114, and prong 112, can be interchangeable or removably coupled to the nasal interface 100.

The interchangeable portions can permit the nasal interface to be adaptable for different types of patients (e.g., neonate, infant, pediatric, adolescent, adult), and different patient characteristics (e.g., sex, age, weight, health condition). For example, a nasal interface 100 can be configured to comprise physical and operational characteristics for a particular patient or condition. The nasal interface 100 can be configured by selecting and coupling a nasal cannula 102, having respective physical and operational characteristics, with a nasal pillow set 104 having respective particular physical and operational characteristics.

Figure 4:
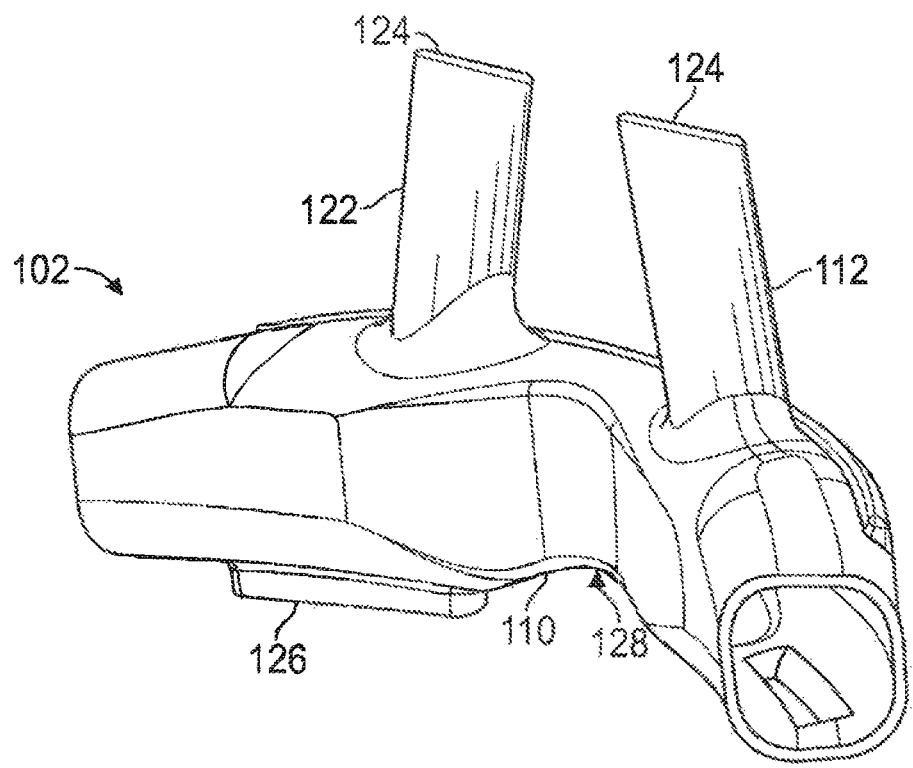
FIGS. 4 and 5 perspective views of a nasal cannula, according to some embodiments.
Figure 5:
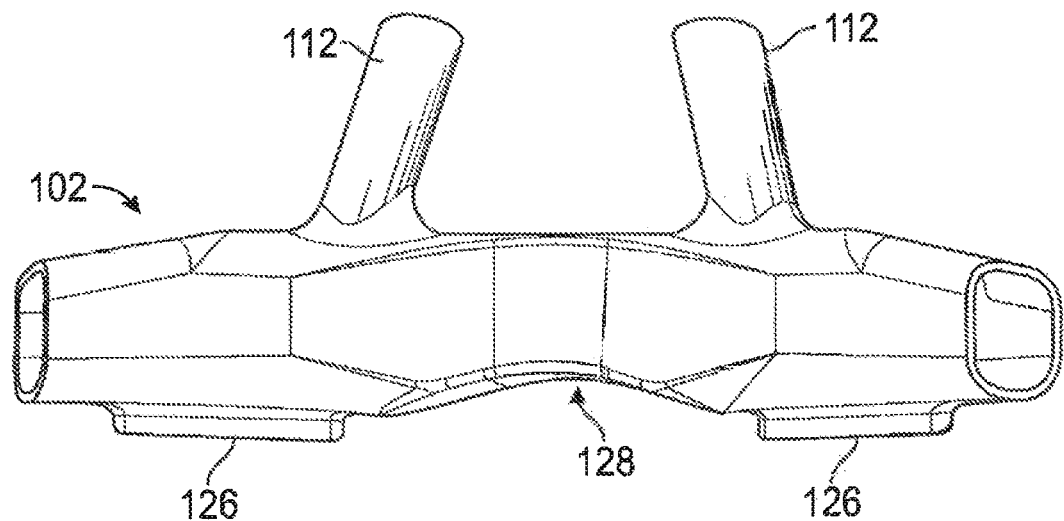

Referring to FIGS. 4 and 5, the nasal cannula 102 can comprise a cannula body 110, and first and second prongs 112. The nasal cannula 102 can comprise a back-side and a front-side that is opposite the back-side. Relative to a patient's anatomy, when the nasal interface 100 is engaged against a patient, the back-side of the nasal cannula 102 can face the patient. The nasal cannula 102 can comprise a top-side and a bottom-side that is opposite the top-side. Relative to a patient's anatomy, when the nasal interface 100 is engaged against a patient, the top-side of the nasal cannula 102 can face any of the patient's nose, nares, and septum.

The nasal cannula 102 can comprise a curved or arch shape configured conform a portion of the patient's face. The back-side of the cannula body 110 can comprise a concave outer surface, and the front-side of the cannula body 110 can comprise a convex surface, such that a cross-sectional profile of the cannula body 110, between the front and back-side, is an arch. The concave outer surface of the back-side can permit the cannula body 110 to extend along a curved portion of the patient's face, e.g., upper lip. The curved or arch cross-sectional profile of the cannula body 110 can permit the prongs 112 to extend from the cannula body 110 and be aligned with a patient's nares.

The nasal cannula 102 can comprise a portion of the bottom-side that is concave, such that the bottom portion extends toward the top-side of the nasal cannula 102. The concave portion 128 of the bottom-side can form a convex surface along the inner passage of the cannula body 110. The concave portion can be positioned along the bottom-side of the cannula body 110, and aligned between the first and second prongs 112. The convex surface along the inner passage of the cannula body 110 can direct a gas toward the prongs 112. In some embodiments, the convex surface along the inner passage of the cannula body 110 directs a gas, receive into the nasal cannula 102, toward any of the first and second prong 112. The convex surface along the inner passage of the cannula body 110 can direct opposing gas flows, received from a first and second gas port 106, toward any of the first and second prong 112.

The nasal cannula 102 can comprise an inner passage that extends between a left and right portion of the cannula body 110. The inner passage can extend between both the left and right portions of the cannula body 110. In some embodiments, the inner passage can be separated between the left and right portions of the cannula body 110 by a wall or septum.

The left portion of the cannula body 110 can comprise a first gas port 106, and the right portion can comprise a second gas port 106. A first and second gas connector 108 (FIGS. 13 and 14) can be coupled to the first and second gas port 106, respectively. A gas supply line, coupled to each of the first and second gas port 106 and/or gas connector 108 can provide an even distribution of force on the nasal interface 100. The distribution of force can prevent movement of the nasal interface 100 toward a single side or direction relative to the patient. In some embodiments, a multi-lumen supply tube can be coupled to the nasal interface 100. The multi-lumen supply tube can comprise a lumen for any of the first and second gas port 106 and the pressure monitoring port 118.

The prongs 112 can extend from the cannula body 110. Each prong 112 can comprise a proximal portion and a distal portion that is opposite the proximal portion. A longitudinal axis can extend through the proximal and distal portions of the prong. The proximal portion of the prong can be coupled to the cannula body 110 and the distal portion of the prong can extend away from the cannula body 110. In some embodiments, first and second prongs 112 extend from the top-side of the cannula body 110. The prong 112 can comprise a passage that extends along the longitudinal axis of the prong 112. The passage can extend between the proximal and distal portions of the prong 112. In some embodiments, the passage can extend from the inner passage of the cannula body 110 through the distal portion of the prong.

The distal portion of the prong 112 can comprise a tip 124. A portion of the passage that extends through the prong 112 can extend though the tip 124. The tip 124 can comprise a distal end portion of the prong 112. The distal end portion of the prong 112 can have a plane that extends through the longitudinal axis of the prong 112. In some embodiments, the tip 124 can comprise a reverse cut so that a plane at the tip 124 is transverse to the longitudinal axis of the prong 112. The reverse cut of the tip 124 can be oriented so that a length of the prong adjacent to the front-side of the nasal cannula 102 is less than a length of the prong 112 adjacent to the back-side of the nasal cannula 102. The reverse cut can prevent contact of the tip 124 with a surface of the patient's nose. For example, the reverse cut can prevent contact of the tip 124 with an outer surface of the patient's nose, or an inner surface of the patient's nares.

In some embodiments, the passage can extend through a portion of the prong 112 that is spaced apart from the tip 124. For example, a passage can extend through a side wall of the prong 112, between the proximal and distal ends of the prong 112. The passage extends along the longitudinal axis of the prong 112, however, the passage can be transverse to the longitudinal axis of the prong 112. In some aspects of the present disclosure, the passage is configured to direct a gas to move out of the prong 112 in a direction that is transverse to the longitudinal axis of the prong 112.

The nasal cannula 102 can comprise a locating member configured to orient the nasal cannula 102 relative to another portion of the nasal interface 100. The locating member can be any of a pin, tab, ridge, groove, opening, notch, and slot. The locating member can comprise any side of the nasal cannula 102, e.g., front, back, top, and bottom-side. The locating member can be a tab that extends from a portion of the cannula body, or a slot that extends along a surface of the cannula body 110. A first portion of the cannula body 110 can comprise a tab and a second portion can comprise a tab. In some embodiments, the locating member can comprise a locating tab 126 that extends from the nasal cannula 102. A left locating tab can extend from an outer surface on the bottom-side, and right locating tab can extend from an outer surface on the bottom-side, of the cannula body 110.

The locating member of the cannula body 110 can be configured to engage with a locating member of the nasal pillow set 104 when the cannula body 110 and nasal pillow set 104 are coupled together.

Figure 6:
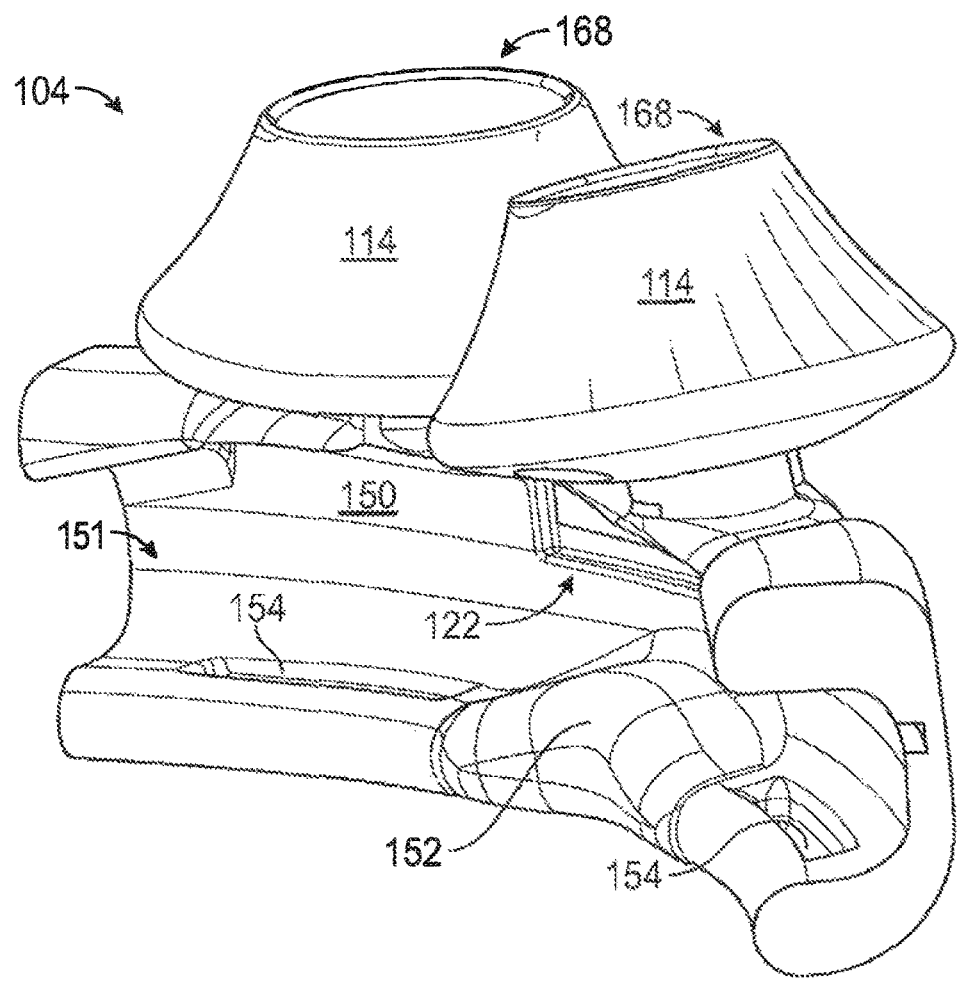
FIGS. 6 and 7 illustrate perspective views of a nasal pillow set, according to some embodiments.
Figure 7:
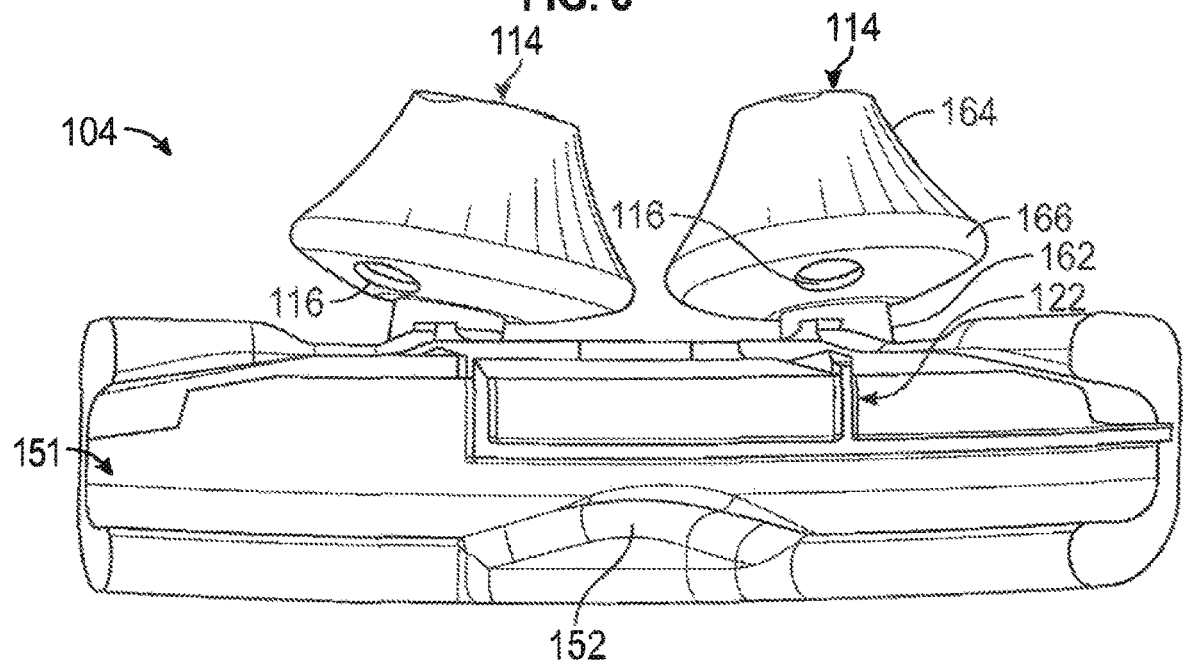

Referring to FIGS. 6 and 7, the nasal pillow set 104 can comprise a pillow body 150 and first and second nasal pillows 114. The nasal pillow set 104 can comprise a back-side and a front-side that is opposite the back-side. Relative to a patient's anatomy, when the nasal interface 100 is engaged against a patient, the back-side of the nasal pillow set 104 can face the patient. The nasal pillow set 104 can comprise a top-side and a bottom-side that is opposite the top-side. Relative to a patient's anatomy, when the nasal interface 100 is engaged against a patient, the top-side of the nasal pillow set 104 can face any of the patient's nose, nares, and septum.

The front-side of the pillow body 150 can comprise a front wall that extends along left and right portions of the nasal pillow set 104. The top-side can comprise a top wall that extends from the front wall. In some embodiments, the top wall can extend from an inner surface of the front wall. The bottom-side can comprise a bottom wall that extends from the front wall. In some embodiments, the bottom wall can extend from an inner surface of the front wall. Portions of the front wall, top wall, and bottom wall of the pillow body 150 can form a channel 151 that extends between left and right portions of the nasal pillow set 104.

The front wall can comprise an inner surface having a curve or arch shape. The inner surface can comprise a concave shape that corresponds with a convex shape of the outer surface of the front-side of the cannula body 110. A portion of the bottom wall of the pillow body 150 can comprise an inner surface having ridge or arch 152. The arch 152 can comprise a convex portion configured to correspond with the concave portion of the outer surface of the bottom-side of the cannula body 110.

The nasal pillow set 104 can comprise a locating member configured to orient the cannula body 110 when the cannula body 110 and nasal pillow set 104 are coupled together. The locating member can comprise any side of the nasal pillow set 104, e.g., front, back, top, and bottom-side. The locating member can be a slot that extends along a portion of the pillow body 150, or a slot that extends along a surface of the pillow body 150. In some embodiments, the locating member can comprise a locating slot 154 that extends along the inner surface of the bottom-side of the pillow body 150. A left locating slot can extend into the inner surface on the bottom-side, and right locating slot can extend into the inner surface on the bottom-side, of the pillow body 150.

The nasal pillows 114 can extend from the pillow body 150. Each nasal pillow 114 can comprise a proximal portion 162 and a distal portion 164 that is opposite the proximal portion 162. A longitudinal axis can extend through the proximal and distal portions of the nasal pillow 114. The proximal portion 162 of the prong can be coupled to the pillow body 150 and the distal portion 164 of the prong can extend away from the pillow body 150. In some embodiments, first and second nasal pillows 114 extend from the top-side of the pillow body 150.

The nasal pillows 114 can comprise an intermediate portion 166 between the proximal portion 162 and distal portion 164. The intermediate portion 166 can comprise an intermediate wall that extends between the proximal portion 162 and distal portion 164 of the pillow 114. The intermediate portion 166 can extend outward from the longitudinal axis of the pillow 114. The distal 164 portion of the pillow 114 can taper from the intermediate portion 166 toward the distal portion 164, such that the proximal and distal portions form a mushroom shape.

A portion of the nasal pillows 114 can engage a patient's nose. In some embodiments, a portion of the nasal pillows 114 can engage against a surface of the nose or nares, e.g., an anterior or posterior surface. An outer surface of the distal portion 164 can engage against a portion of the patient's nose that is proximal or adjacent to the nares. In some aspects, a portion of the nasal pillows 114 can extend into the nares. For example, the distal portions 164 of the nasal pillows 114 can extend into the patient's nares.

The nasal pillow 114 can comprise a passage that extends between the proximal and distal portions. The passage can extend from proximal portion 162 to the distal portion 164 of the nasal pillow 114. The passage can comprise a pillow aperture 168 that extends through a portion of the nasal pillow 114. The pillow aperture 168 can extend through the distal portion 164, such that a passage extends from a pillow cavity within the distal portion of the nasal pillow 114 to an outer surface of the nasal pillow 114. In some embodiments, the tip 124 comprises the pillow aperture 168.

The pillow 114 can comprise a pressure relief port 116. The pressure relief port 116 can comprise an aperture that extends through a portion of the nasal pillow 114. The aperture can extend through any of the proximal portion 162, distal portion 164, and intermediate portion 166. The aperture can extend through the intermediate wall, such that a passage extends from a cavity within the distal portion of the nasal pillow 114 to an outer surface of the nasal pillow 114. The passage can extend between a cavity, formed between an outer surface of the prong 112 and the nasal pillow 114, to the ambient atmosphere around the nasal pillow 114. In some embodiments, the pressure relief port aperture extends through a portion of the nasal pillow 114 that is aligned with the back-side portion of the nasal pillow set 104.

Figure 8:
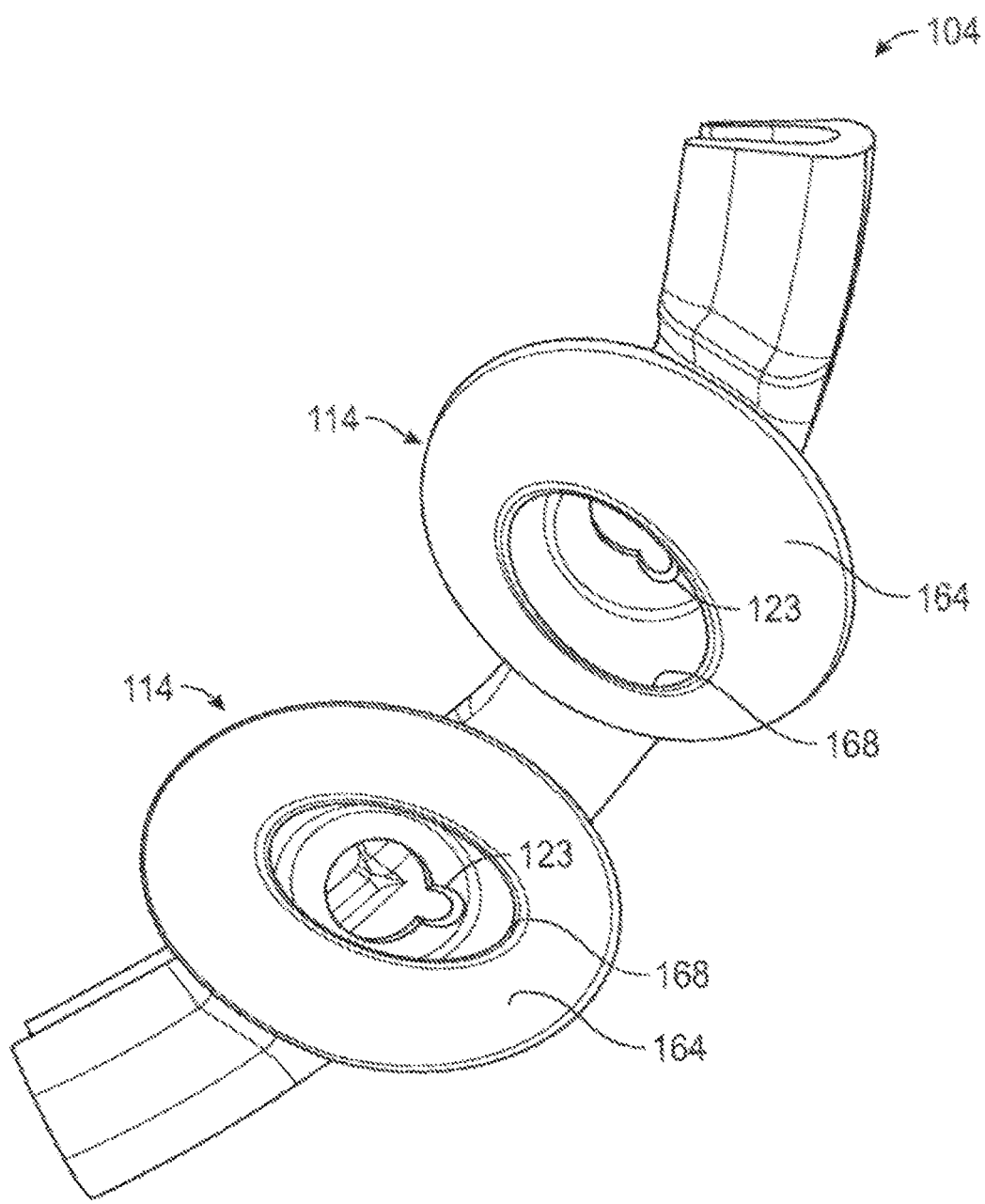
FIG. 8 illustrates a top view of a nasal pillow set, according to some embodiments.
Figure 9:
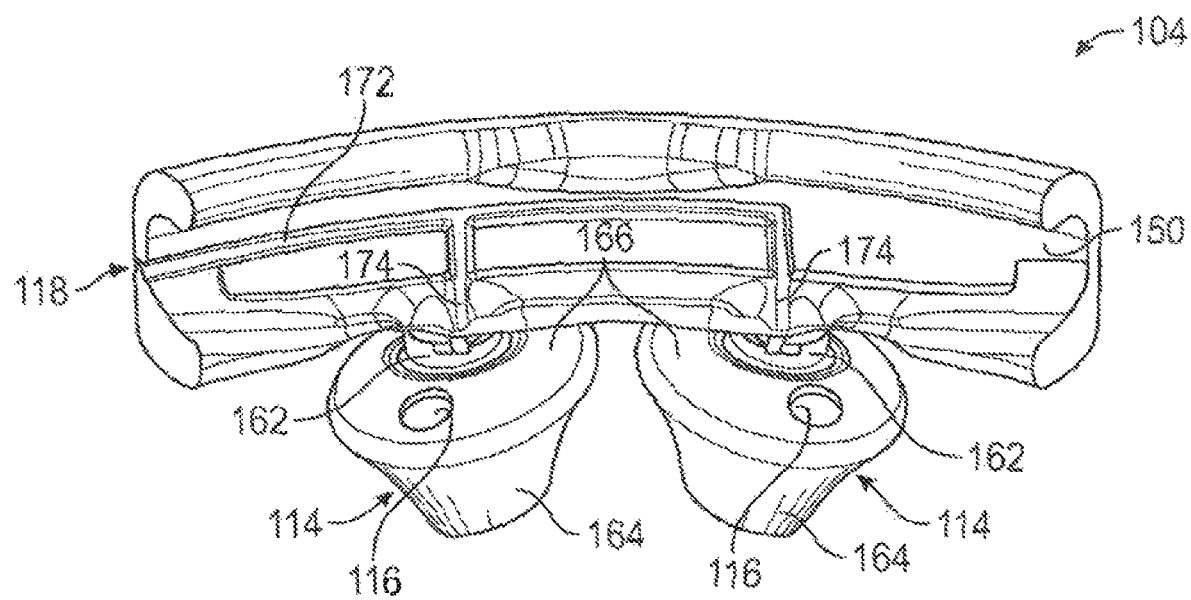
FIGS. 9 and 10 illustrate bottom views of a nasal pillow set, according to some embodiments.
Figure 10:
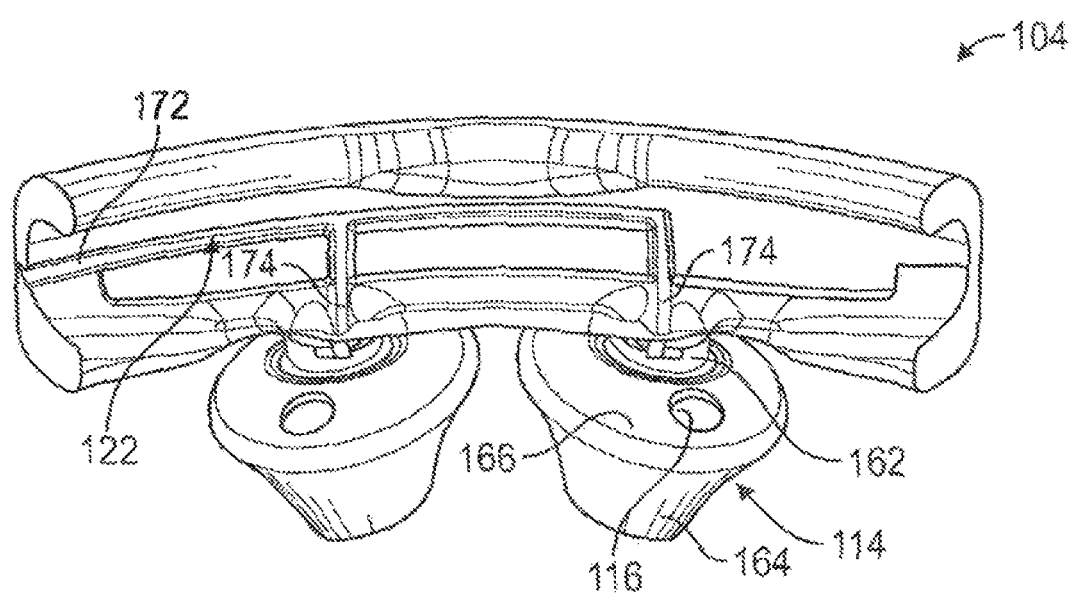
Figure 11:
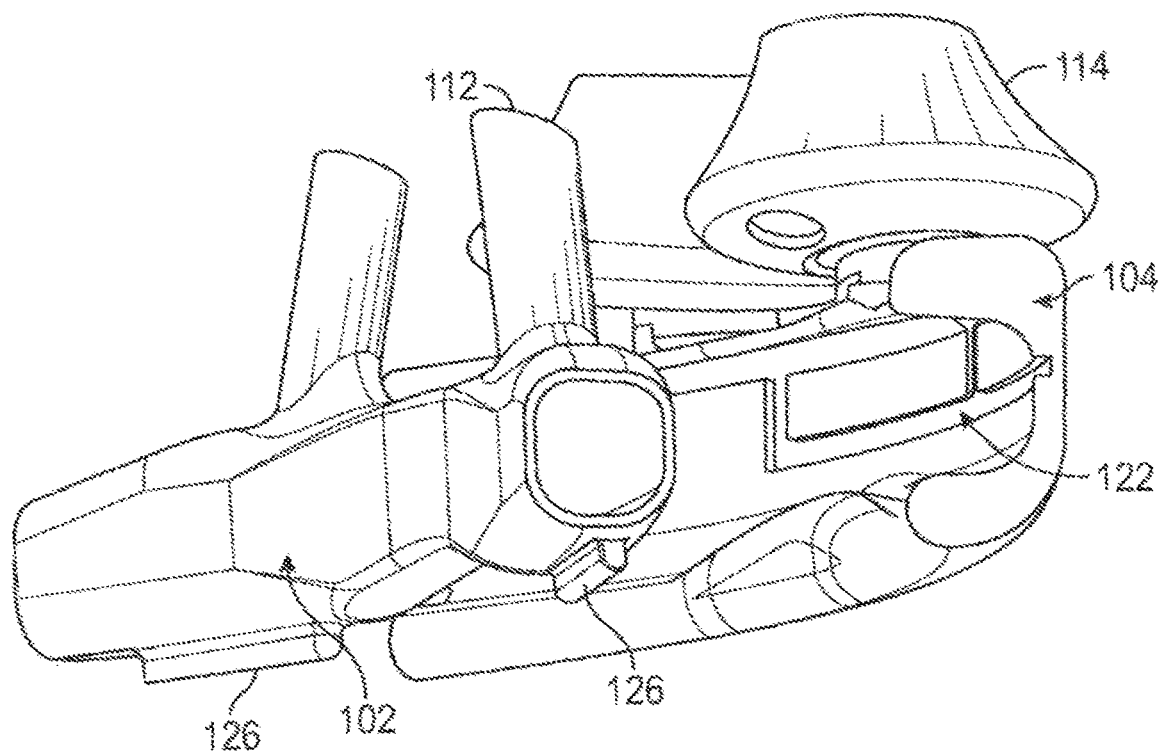
FIG. 11 illustrates an exploded view of a nasal interface, according to some embodiments.
Figure 12:
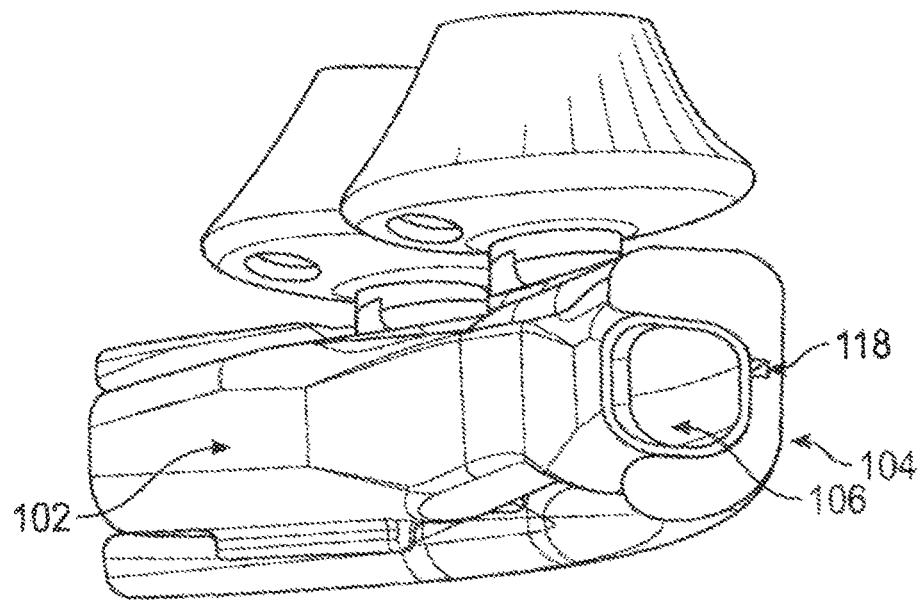
FIG. 12 illustrates a side view of a nasal interface, according to some embodiments.

Referring to FIGS. 8-10, the nasal pillow set 104 can comprise a portion of the pressure passage 122. The pressure passage 122 can extend from an outer surface of the nasal pillow set 104 to each of the nasal pillows 114. A portion of the pressure passage 122 can extend from the pressure monitoring port 118 toward a nasal pillow 114. The pressure passage 122 can extend from the pressure monitoring port 118 to each of the first and second nasal pillow 114. In some embodiments, the pillow body 150 comprises a main portion 172 of the pressure passage, a first branch 174 of the pressure passage that extends to a first pillow 114, and a second branch 174 of the pressure passage that extends to a second pillow 114. The first and second branch portions of the pressure passage 122 can extend into the cavity of the nasal pillows 114.

In some embodiments, the nasal interface 100 can comprise separate pressure passages. A first pressure passage can extend to a first nasal pillow 114, and a second pressure passage can extend to a second nasal pillow 114. The separate pressure passages can extend from a single pressure monitoring port, or first and second pressure passages can extend from first and second pressure monitoring ports, respectively. The first and second pressure monitoring ports can be positioned together or separated. The first and second pressure monitoring ports can be positioned on opposing end portions of the nasal interface 100.

A portion of the pressure passage 122 can comprise a channel 123 or groove that extends along the nasal pillow set 104, such that an enclosed passage is formed when the nasal cannula 102 is coupled with the nasal pillow set 104. The channel 123 can extend into the inner surfaces of the front and top walls of the pillow body 150. The channel 123 of the first and second branch portions of the pressure passage 122 can extend from the pillow body 150 to the cavity of each nasal pillow 114. The channel 123 of the first and second branch portions can extend along an inner surface of the nasal pillow passage, from the proximal portion 162 toward the cavity of the distal portion 164 of the nasal pillow 114.

The nasal cannula 102 can be coupled with the nasal pillow set 104 by directing the prongs toward the inner surface of the pillow body top wall. The nasal cannula 102 can be moved toward the nasal pillow set 104 so that each of the first and second prongs 112 is inserted into the passage of the first and second nasal pillows 114, respectively. The prongs 112, when inserted through the nasal pillows 114, can extend from the proximal portion 162 toward the distal portion 164 of the nasal pillow 114. In some embodiments, the prong 112 extends from the proximal portion 162 toward the pillow aperture 168, such that a gas is directed from the nasal cannula 102 toward the nares of a patient engaged against the nasal pillows 114.

The tip 124 of the prong can extend proximal to the pillow aperture 168. In some embodiments, the tip 124 of the prong is positioned within the cavity of the pillow 114, proximal to the pillow aperture 168. The prong 112 can be positioned so that the tip 124 does not extend through the pillow aperture 168, thereby preventing contact of the prong 112 with the patient.

When the nasal cannula 102 is coupled with the nasal pillow set 104, portions of the outer surface of the top, front, and bottom-sides of the nasal cannula 102 can engage against portions of the inner surface of the top, front, and bottom-sides of the nasal pillow set 104. When the nasal cannula 102 is coupled with the nasal pillow set 104, a locating tab 126, e.g., first and second tab 126, of the nasal cannula 102 can extend into a locating slot 154, e.g., first and second slot 154, of the pillow body 150.

Referring to FIGS. 9 and 10, a portion of the pressure passage 122 can be defined when the nasal cannula 102 is coupled with the nasal pillow set 104. The outer surfaces of the nasal cannula 102 can engage inner surfaces of the nasal pillow set 104 to enclose the channel 123 and seal the pressure passage 122. The outer surface of the front-side of the nasal cannula 102 can enclose the main portion 172 of the pressure passage 122, and the outer surface of the front and top-sided of the nasal cannula 102 can enclose the first and second branch portions 172 and 174 of the pressure passage 122. The outer surface of the prongs 112 can enclose the first and second branch portions 172 and 174 of the pressure passage 122 that extend along the nasal pillows 114.

In some embodiments, any of the nasal cannula 102 and the nasal pillow set 104 can comprises portions of a channel or groove of the pressure passage 122, such that an enclosed passage is formed when the nasal cannula 102 is coupled with the nasal pillow set 104.

In operation, the nasal pillows 114 can be engaged with the nares of a patient. A gas can be directed from the cannula body 110 to the nasal pillows 114, such that the patient can breathe the gas in through their nose. The pressure relief ports 116 permit the egress of excessive gas flow, including the patient's exhalation, from the nasal interface 100. The aperture of the pressure relief ports 116 can comprise a size that provides a resistance to the egress of gas flow from the nasal interface 100. The pressure relief ports 116, along with the flow being directed through the cannula body 110 toward the patient, can provide control of the pressure within the airway of the patient.

Features of the nasal interface 100, including the pressure relief ports 116, can provide a safety feature for patients. For example, pressure delivered to the lungs of an infant patient can be a balance of the diameter of the prongs 112, and the area of their infant patient's nasal passages. A relationship between the features of the nasal interface 100 can vary between patients, and even among the same patient type, e.g., infants. The relationship of the features of the nasal interface 100 can vary depending upon the depth of insertion of prongs and/or nasal pillows into the patient's nares. The relationship of the features can change over time, and even on a minute-to-minute basis. However, the pressure relief ports 116 can provide a fixed and known size for egress of gas, such that variations in the patient's nasal passage are not a variable factor in affecting the airway pressure.

To engage a respiratory device to a patient's nose or mouth a mounting head harness can be coupled to the respiratory device can be worn on the patient's head. The mounting head harness can guide a portion of tubing, e.g., a cannula tube, gas supply line, or a pressure sense line, relative to the patient's head. The mounting head harness can enable the tubing to pass at points closest to the centerline of the patient's head and in many cases inside a contact distance of the widest section of the patient's skull.

Referring to FIGS. 15-19, embodiments of a mounting head harness 500 are illustrated. The mounting head harness 500 is shown with a nasal interface 100 illustrated schematically. However, the mounting head harness 500 can be implemented with any respiratory device.

The mounting head harness 500 can comprise a guide 502. The guide can extend along a patient's head, from a proximal portion adjacent to the ear, toward a distal portion adjacent to the cheek. A proximal end portion of the guide 502 can be aligned with patient's ear but not extend along the patient's head below the ear. A portion of the guide 502 can extend over, but not touching the patient's ear. A distal end portion of the guide 502 can extend toward a nose and/or mouth of a patient. The distal end portion of the guide 502 can be separated from the respiratory device. In some embodiments, tubing 20 extends between the guide 502 and the respiratory device. The mounting head harness 500 can comprise first and second guides 502 that extend along the left and ride sides of the patient's head, respectively.

The guide 502 can comprise a semi-rigid material to permit the guide 502 to conform to a shape of the patient's head. For example, the guide 502 can be biased toward the patient's head by a strap of the mounting head harness 500. In some embodiments, the guide 502 can be manufactured comprising a curvature to conform to a shape of a head. For example, an inner surface of the guide 502, configured to engage against a patient's head, can comprise a curved or concaved portion.

The mounting head harness 500 can comprise a tubing retainer to engage a portion of a tubing 20. The tubing retainer can engage a portion of a tubing 20 to retain the tubing relative to the mounting head harness 500. The tubing retainer can be moveable relative to the mounting head harness 500 to permit orientation of the tubing. In some aspects, the tubing retainer can permit a positional setting of the nasal interface 100, such that a prong is oriented relative to the patient's nares, e.g., distance and/or angle. In some embodiments, the tubing retainer can be locked in an orientation when a portion of tubing 20 is coupled with the tubing retainer. In some embodiments, the mounting head harness 500 can comprise a plurality of tubing retainers.

The tubing retainer can comprise a tubing clip 510 to retain a portion of tubing with the mounting head harness 500. A tubing clip 510 can be positioned along any of the proximal and distal portions of the guide 502. In some embodiments, the guide 502 comprises one or more tubing clips 510 along any of the proximal and distal portions. The guide 502 can comprise three tubing clips 510, positioned along the proximal and distal portions.

The tubing clip 510 can comprise a base portion and a retainer portion. The base portion can be coupled to the guide 502. The retainer portion can be configured to engage with a portion of a tubing 20. In some embodiments, the retainer portion can comprise an arm configured to engage a portion of a tubing 20. The retainer portion can comprise a pair of arms configured to be biased apart when a portion of tubing is inserted between the arms. In some embodiments, the tubing clip 510 can comprise any of a clip, hook, loop, and strap.

The tubing clip 510 can permit an orientation or positional setting of the tubing and/or nasal interface 100. One or more tubing clip 510 can be oriented such that a prong is at a desired angle to the patient's nares. Tubing can be locked in tubing clips 510 to prevent the tubing and cannula from rotating out of the nares. The tubing clips 510 can permit the positioning of the nasal interface 100 at a distance from the nasal septum to minimize contact and septal injury.

The guide 502 can comprise an attachment member 520 to permit attachment of a strap. The attachment member 520 can comprise any of a tang, tab, clip, hook, and loop. In some embodiments, the attachment member 520 comprises a tab that extends from the guide 502. A first tab can extend from the proximal portion of guide 502 aligned toward a back portion of the patient's head, and a second tab can extend from the intermediate portion of guide 502 aligned toward a middle portion of the patient's head. The tab can comprise a slot configured to receive a portion of a strap to retain one or more guide 502 relative to the patient's head.

A first strap 530 can extend along a back portion of the patient's head, between a first tab of a first guide, and a first tab of a second guide. A second strap 540 can extend along a top portion of the patient's head, between a second tab of a first guide, and a second tab of a second guide.

The attachment member can comprise a sleeve 525 configured to receive a portion of the guide 502. The guide 502 can be inserted into the sleeve so that a proximal portion of the sleeve 525 can be aligned with the intermediate portion of the guide 502, and a distal portion of the sleeve 525 can be aligned with a distal portion of the guide 502.

A first and second strap 530 and 540 can extend from the sleeve to retain one or more guide 502 relative to the patient's head. The first and second strap 530 and 540 can extend from a proximal portion of the sleeve, adjacent to the intermediate portion of the guide 502.

Any of the strap 530 and 540 and the sleeve 525 can comprise an elastic or non-elastic material. Portions of the strap 530 and 540 and the sleeve 525 can comprise a mesh material configured to conform to a portion of the guide 502 or patient. Portions of the strap 530 and 540 and the sleeve 525 can comprise a fastener, e.g., a hook and loop fastener, to permit coupling of a strap and/or sleeve with the guide 502.

The mounting head harness 500 can maintain a position of a respiratory device and tubing. The mounting head harness 500 can maintain engagement of nasal interface with a patient's nose. The mounting head harness 500 can reduce a force required to hold a cannula or portion of the nasal interface relative to a patient, thereby preventing septal injury. The mounting head harness 500 can prevent a portion of the nasal interface from disengaging or slipping out of a nose or becoming obstructed on the upper lip. For example, the mounting head harness 500 can prevent rolling of a cannula or nasal interface on the upper lip of a patient. The mounting head harness 500 can also prevent a cannula tube from engaging patient's skin and causing irritation.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A nasal interface comprising: a pillow body comprising a nasal pillow having an pillow opening and a pillow cavity that extends from the pillow opening into the nasal pillow, wherein the nasal pillow is configured to engage a nose to fluidly coupled to the pillow cavity with a nostril of the nose; a cannula body comprising a prong that extends into and is fluidly coupled to the pillow cavity; a pressure monitoring port fluidly coupled to the pillow cavity; and a pressure relief port coupled to the pillow cavity.

Clause 2. The nasal interface of Clause 1, wherein the pressure relief port comprises an aperture through the pillow body.

Clause 3. The nasal interface of Clause 2, wherein the aperture extends between the pillow cavity and an ambient atmosphere adjacent an outer surface of the nasal interface.

Clause 4. The nasal interface of Clause 2, wherein the aperture extends through a portion of the nasal pillow opposite the pillow opening.

Clause 5. The nasal interface of Clause 1, wherein the pressure monitoring port comprises a passage coupled to the pillow body.

Clause 6. The nasal interface of Clause 1, wherein the nasal pillow extends away from an outer surface of the pillow body.

Clause 7. The nasal interface of Clause 1, wherein the cannula body comprises a first prong and a second prong.

Clause 8. The nasal interface of Clause 7, wherein the cannula body comprises a first gas port and second gas port fluidly coupled to the first and second prong.

Clause 9. The nasal interface of Clause 8, wherein each of the first and second gas ports extend through opposing portions of the cannula body.

Clause 10. The nasal interface of Clause 1, wherein the prong extends into the pillow cavity, the prong configured to direct a gas toward the nostril of the nose.

Clause 11. The nasal interface of Clause 1, wherein the prong extends toward the pillow opening.

Clause 12. The nasal interface of Clause 1, wherein the pillow body comprises a cavity configured to engage with the cannula body.

Clause 13. The nasal interface of Clause 1, wherein the pillow body comprises a pressure passage coupled to the pressure monitoring port.

Clause 14. The nasal interface of Clause 13, wherein a portion of the pressure passage comprises a channel that extends along a surface of the pillow body configured to be engaged by the cannula body.

Clause 15. The nasal interface of Clause 14, wherein the channel is enclosed by engagement of the cannula body against the pillow body.

Clause 16. The nasal interface of Clause 13, wherein a portion of the pressure passage comprises a channel that extends along a portion of the nasal pillow, and wherein the prong engages against the nasal pillow to enclose the channel.

Clause 17. The nasal interface of Clause 1, wherein the cannula body comprises a locating tab that extends from an outer surface of the cannula body.

Clause 18. The nasal interface of Clause 17, wherein the pillow body comprises a locating slot configured to receive the locating tab.

Clause 19. A nasal interface assembly comprising: a nasal interface comprising: a pillow body comprising a nasal pillow having an pillow opening and a pillow cavity that extends from the pillow opening into the nasal pillow, wherein the nasal pillow is configured to engage a nose to fluidly couple the pillow cavity with a nostril of the nose; a cannula body comprising a prong coupled to the pillow cavity, wherein the prong is configured to direct a gas out of the cannula body; a pressure monitoring port fluidly coupled to the pillow cavity; and a pressure relief port coupled to the pillow cavity; and a gas supply line fluidly coupled to the cannula body; and a pressure sense line fluidly coupled to the pressure monitoring port.

Clause 20. The nasal interface assembly of Clause 19, comprising a mounting head harness configured to couple the nasal interface with a nose of a patient.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A nasal interface comprising:
   a pillow body comprising a nasal pillow having a pillow opening and a pillow cavity that extends from the pillow opening into the nasal pillow, wherein the nasal pillow is configured to engage a nose to fluidly couple the pillow cavity with a nostril of the nose, and a pressure channel extending into an inner surface of the pillow body;
   a cannula body comprising a prong having a distal end that extends into and is fluidly coupled to the pillow cavity;
   a pressure monitoring port comprising a pressure passage, wherein the pressure passage is formed by engagement of an outer surface of the cannula body against the inner surface of the nasal pillow along the pressure channel to enclose the pressure passage therebetween, and the pressure passage extends into and is in fluid communication with the pillow cavity with a distal end of the pressure passage positioned proximal to the distal end of the prong; and
   a pressure relief port coupled to the pillow cavity.

2. The nasal interface of claim 1, wherein the pressure relief port comprises an aperture through the pillow body.

3. The nasal interface of claim 2, wherein the aperture extends between the pillow cavity and an ambient atmosphere adjacent an outer surface of the nasal interface.

4. The nasal interface of claim 2, wherein the aperture extends through a portion of the nasal pillow opposite the pillow opening.

5. The nasal interface of claim 1, wherein the nasal pillow extends away from an outer surface of the pillow body.

6. The nasal interface of claim 1, wherein the cannula body comprises another prong.

7. The nasal interface of claim 6, wherein the cannula body comprises a first gas port fluidly coupled to the prong, and a second gas port fluidly coupled to the another prong.

8. The nasal interface of claim 7, wherein each of the first and second gas ports extend through opposing portions of the cannula body.

9. The nasal interface of claim 1, wherein the prong extends into the pillow cavity, the prong configured to direct a gas toward the nostril of the nose.

10. The nasal interface of claim 1, wherein the prong extends toward the pillow opening.

11. The nasal interface of claim 1, wherein the pillow body comprises a cannula body channel configured to receive the cannula body therein.

12. The nasal interface of claim 1, wherein the pillow body comprises the pressure passage.

13. The nasal interface of claim 1, wherein the pressure channel extends along another surface of the pillow body configured to be engaged by the cannula body.

14. The nasal interface of claim 13, wherein the pressure channel is enclosed by engagement of the cannula body against the another surface of the pillow body.

15. The nasal interface of claim 1, wherein the cannula body comprises a locating tab that extends from an outer surface of the cannula body.

16. The nasal interface of claim 15, wherein the pillow body comprises a locating slot configured to receive the locating tab.

17. The nasal interface of claim 1, wherein the distal end of the pressure passage is proximal to the pillow opening.

18. The nasal interface of claim 1, wherein the pillow cavity comprises a cross-sectional width that decreases from an intermediate portion of the nasal pillow to a distal end of the nasal pillow comprising the pillow opening.

19. A nasal interface assembly comprising:
   a nasal interface comprising:
      a pillow body comprising a nasal pillow having a pillow opening and a pillow cavity that extends from the pillow opening into the nasal pillow, wherein the nasal pillow is configured to engage a nose to fluidly couple the pillow cavity with a nostril of the nose, and a pressure channel extending into an inner surface of the pillow body;
      a cannula body comprising a prong coupled to the pillow cavity, wherein the prong comprises a distal end that is configured to direct a gas out of the cannula body;
      a pressure monitoring port comprising a pressure passage, wherein the pressure passage is formed by engagement of an outer surface of the cannula body against the inner surface of the nasal pillow along the pressure channel to enclose the pressure passage therebetween, and the pressure passage extends into and is in fluid communication with the pillow cavity with a distal end of the pressure passage positioned proximal to the distal end of the prong; and
      a pressure relief port coupled to the pillow cavity; and
   a gas supply line fluidly coupled to the cannula body; and
   a pressure sense line fluidly coupled to the pressure monitoring port.

20. The nasal interface assembly of claim 19, comprising a mounting head harness configured to couple the nasal interface with a nose of a patient.

* * * * *